United States Patent
Mane et al.

(10) Patent No.: US 9,541,482 B2
(45) Date of Patent: Jan. 10, 2017

(54) DEVICE AND METHOD FOR BILIRUBIN PHOTOISOMERIZATION TO REDUCE LABORATORY TEST INTERFERENCE

(71) Applicants: Viraj Mane, Toronto (CA); Edward Wong, Alexandria, VA (US)

(72) Inventors: Viraj Mane, Toronto (CA); Edward Wong, Alexandria, VA (US)

( * ) Notice: Subject to any disclaimer, the term of this patent is extended or adjusted under 35 U.S.C. 154(b) by 0 days.

(21) Appl. No.: 14/584,686

(22) Filed: Dec. 29, 2014

(65) Prior Publication Data
US 2015/0153260 A1 Jun. 4, 2015

Related U.S. Application Data

(63) Continuation of application No. 13/925,757, filed on Jun. 24, 2013, now abandoned.

(60) Provisional application No. 61/663,333, filed on Jun. 22, 2013.

(51) Int. Cl.
| | |
|---|---|
| *G01N 33/70* | (2006.01) |
| *G01N 1/44* | (2006.01) |
| *A61M 1/36* | (2006.01) |
| *G01N 33/92* | (2006.01) |
| *A61M 1/16* | (2006.01) |

(52) U.S. Cl.
CPC .............. *G01N 1/44* (2013.01); *A61M 1/3681* (2013.01); *G01N 33/70* (2013.01); *G01N 33/92* (2013.01); *A61M 1/1698* (2013.01); *Y10T 436/147777* (2015.01); *Y10T 436/25375* (2015.01)

(58) Field of Classification Search
CPC .......... G01N 1/44; G01N 33/70; G01N 33/92
See application file for complete search history.

(56) References Cited

U.S. PATENT DOCUMENTS

| | | | |
|---|---|---|---|
| 4,069,016 A | 1/1978 | Wu | |
| 4,291,121 A | 9/1981 | Acquati | |
| 4,444,190 A * | 4/1984 | Mutzhas | A61N 5/0621 250/503.1 |
| 4,890,997 A * | 1/1990 | Beins | G01N 1/36 264/279.1 |
| 5,792,214 A * | 8/1998 | Larsson | A61N 5/0621 362/130 |
| 6,596,016 B1 * | 7/2003 | Vreman | A61N 5/0621 128/903 |
| 2005/0015040 A1 * | 1/2005 | Wuepper | A61M 1/3472 604/5.01 |

\* cited by examiner

*Primary Examiner* — Leslie Deak
*Assistant Examiner* — Kai Weng
(74) *Attorney, Agent, or Firm* — Juneau & Mitchell

(57) ABSTRACT

Provided are a device and method for using bilirubin photoisomerization to reduce bilirubin interference with laboratory blood tests for other chemical analytes.

5 Claims, 4 Drawing Sheets

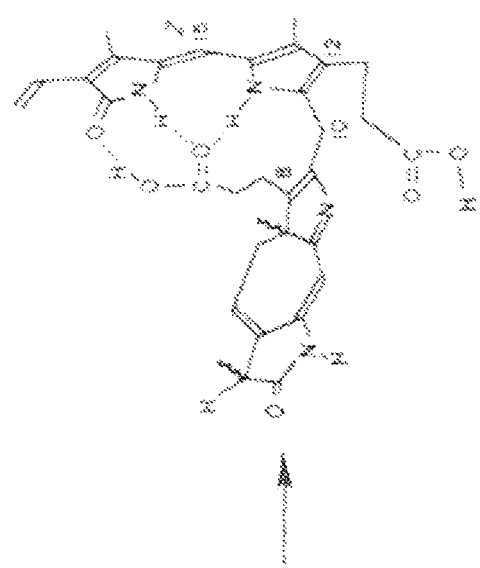
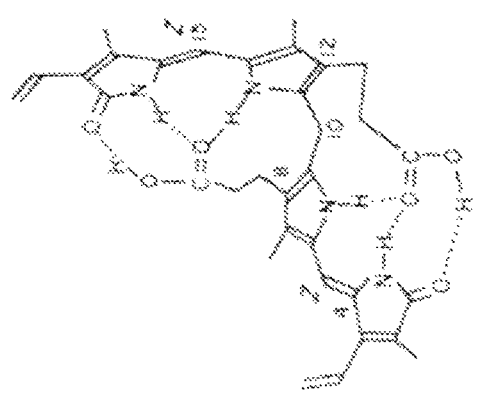
FIG. 1A
FIG. 1B

DEVICE AND METHOD FOR BILIRUBIN PHOTOISOMERIZATION TO REDUCE LABORATORY TEST INTERFERENCE

CROSS REFERENCE TO RELATED APPLICATIONS

This patent application claims priority to U.S. patent application Ser. No. 13/925,757, filed on Jun. 24, 2013, and thereby to U.S. patent application 61/663,333, filed on Jun. 22, 2012.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The present invention relates to a device and method for bilirubin photo-isomerization to reduce laboratory test interference in mammalian fluids.

Background of the Invention

Bilirubin has spectral and chemical properties that lead to interference with the measurement of common clinical laboratory analytes in patient samples. For example, bilirubin is known to interfere with fluid tests for the measurement of creatinine, cholesterol, and triglycerides. Spectral interference is caused when absorption of a certain wavelength of light is similar between bilirubin and the analyte of interest, thereby artificially increasing the apparent absorption profile of the analyte. Alternatively, bilirubin may absorb or "quench" the signal emanating from an analyte, artificially suppressing the signal. Chemical interference is caused when bilirubin reacts with chemical intermediaries designed to detect an analyte, resulting in compromised measurement of the analyte. These forms of interference may artificially suppress or inflate the values of important diagnostic analytes in a patient sample, reducing the accuracy of clinical chemistry testing. This loss of accuracy may lead serious diagnostic errors and even the administration of inappropriate medical treatments or interventions, which may have unwanted and/or harmful effects on the patient.

Bilirubin is primarily a breakdown byproduct of hemoglobin which is released upon death and decomposition of red blood cells. Jaundice is a clinical condition experienced by many newborn babies as well as children and adults stricken with certain diseases where abnormally high levels of bilirubin have accumulated in their bodies. Its most pronounced symptom is yellow coloring of the skin and eyes.

Normally, bilirubin is conjugated with glucuronic acid in the liver so that it can be solubilized and eliminated from the body through the bile. However, several of the proteins and enzymes that perform this function are not present at the necessary levels in newborns and in certain pediatric and adult diseases. This leads to a rise in bilirubin levels in the blood. Since the bilirubin is not water-soluble it tends to accumulate in body tissues, thereby causing the yellow coloration.

Bilirubin has the chemical structure shown in FIG. 1A. The carboxyl groups form hydrogen bonds with nearby nitrogen atoms, which hides the hydrophilic moieties and increases the molecule's overall hydrophobicity. Bilirubin's hydrophobicity makes it dangerous because it will readily absorb into tissue and cross the blood/brain barrier.

The danger of high levels of bilirubin is that it can be neurotoxic, a condition known as kernicterus. If levels remain elevated there can be irreversible nerve damage, or even death.

Light-mediated isomerization (referred to as phototherapy in therapeutic settings) initiates a structural isomerization of bilirubin to lumirubin, an isomer with substantially different chemical and light absorption properties than bilirubin. Among other differences, the isomerization of bilirubin yields a free carboxyl group that makes lumirubin much more hydrophilic than bilirubin. The magnitude of phototherapy-mediated conversion of bilirubin to lumirubin increases with the intensity of the light, so a device designed to generate light of the proper wavelength and focus that light directly on subject fluid samples will yield substantial benefits in the speed and efficiency of the preparation of fluids for "clean" chemical analyte testing. Since testing labs, in hospitals and outside hospitals, tend to handle scores or hundreds of samples a day, a device maximizing efficiency by reducing time to process bilirubin cleansing will yield a substantial economic benefit to the testing company.

Light-mediated photoisomerization, including phototherapy, is considered to be extremely safe. The only potential risk is damage to the eyes by the intense light. Therefore, it is highly recommended that the eyes of any photoisomerization operators and/or recipients be protected appropriately. Otherwise, no significant side effects of phototherapy have been documented.

The most efficient wavelength for the isomerization of bilirubin is approximately 450 nm, whether applied to the cleansing of fluid samples for testing or the treatment of jaundice. Wavelengths that fall within the range of 400 nm-500 nm, and more specifically 445 nm-475 nm are known to effect isomerization. In addition, a light intensity of at least 6 microWatts per square centimeter per nanometer of light wavelength is needed for phototherapy. This intensity is equivalent to 2.7 milliwatts per square centimeter of 450 nm wavelength light.

Hyperbilirubinemia, an elevation in bilirubin circulating in the blood, can arise from both acute and congenital circumstances. Bilirubin is a natural byproduct of the metabolism of hemoglobin derived from aged or injured red blood cells. Infant hyperbilirubinemia (neonatal jaundice) is common but easily treated by placing the infant under blue lights, known as phototherapy. Unmanaged hyperbilirubinemia, however, leads to kernicterus (brain damage, ataxia) and early mortality.

Solitary bilirubin is insoluble in the blood and cannot be efficiently excreted in this form. It is therefore conjugated and solubilized by the enzyme uridine diphosphate glycosyltransferase 1-A1 (UGT1A1), allowing excretion through the feces and urine. Unconjugated hyperbilirubinemia is a hallmark of Crigler-Najjar Syndrome (CNS) Type 1, a genetic deficiency of UGT1A1. The current standard treatment for CNS is phototherapy, which is conducted within a bed or chamber fitted with blue lights (wavelength of approximately 450 to 530 nm). Light of this wavelength initiates a photo-isomerization reaction which converts unconjugated bilirubin into an isomer known as lumirubin, which is water soluble and readily excreted. However, the onset of puberty is characterized by thickening and pigmentation of the skin, accompanied by a decrease in the body's surface area:volume ratio. These changes represent barriers to light penetration into circulating blood (which contains the majority of bilirubin). Therefore, the efficacy of phototherapy decreases substantially following puberty. Consequently, older CNS patients are particularly susceptible to elevated bilirubin in the blood, which may interfere with clinical chemistry measurements taken on patient samples.

As mentioned above, bilirubin is a byproduct of the natural turnover and destruction of red blood cells, which releases hemoglobin into the blood. Breakdown of hemoglobin releases a heme group which is further catabolized into bilirubin. At physiological blood pH (around pH 7.4), bilirubin's hydrophilic domain is masked by hydrogen bonding, reducing its solubility. However, bilirubin is conjugated to glucuronic acid in the endoplasmic reticulum of hepatocytes by the enzyme uridine diphosphate glycosyltransferase 1-A1 (UGT1A1), disrupting the hydrogen bonds. The resulting configurational and structural changes facilitate bilirubin solubilization and excretion through the liver, kidneys, and intestines. Crigler-Najjar Syndrome (CNS) Type 1 patients lack UGT1A1 activity due to a genetic abnormality and suffer from chronic unconjugated hyperbilirubinemia. While the normal level of unconjugated bilirubin in the blood is 0.2-0.9 mg/dL, CNS patients have ≥20 mg/dL of bilirubin in their blood.

It should be noted that disorders similar to CNS also present in the veterinary context, and that the device and methods described herein apply to all blood samples from mammals, whether human or animal. The same benefits regarding fluid testing protocols for human patients described herein will also apply in the veterinary context.

What is needed is a device and method for processing high-bilirubin fluid samples being tested for other chemical analytes for diagnostic purposes in order to reduce or remove the bilirubin from such samples and thereby minimize the bilirubin's interference with the measurement of such other chemical analytes.

BRIEF SUMMARY OF THE INVENTION

This device reduces bilirubin interference via blue light exposure.

In a preferred embodiment, an extracorporeal photoisomerization apparatus for photoisomerization of bilirubin in mammalian fluids, said apparatus comprising a chamber consisting of a bottom panel and at least four side panels having reflective interior surfaces, wherein one or more of the bottom panel and/or one or more side panel comprises one or more holes, a blue light centered within each such hole and facing towards the interior of the chamber, one or more stands configured within the chamber to hold containers of fluid for irradiation, a means for turning the blue light(s) on or off, and a means for delivering electricity to the one or more blue lights.

In another preferred embodiment extracorporeal photoisomerization apparatus as described herein, further comprising a removable top panel with a reflective interior surface.

In another preferred embodiment extracorporeal photoisomerization apparatus as described herein, wherein the removable top panel comprises one or more holes, with a blue light centered within each such hole and facing towards the interior of the chamber.

In another preferred embodiment extracorporeal photoisomerization apparatus as described herein, further comprising wherein the blue lights irradiate at a wavelength between 450 to 530 nm.

In another preferred embodiment extracorporeal photoisomerization apparatus as described herein, further comprising wherein the blue lights irradiate at a light intensity level of at least 6 microWatts µW/cm2/nm of light wavelength.

In another preferred embodiment extracorporeal photoisomerization apparatus as described herein, further comprising wherein the blue lights comprise a transparent cover.

In another preferred embodiment, a process of chemical analysis of mammalian fluids comprising (i) collecting a fluid sample from a mammal; (ii) photoisomerizing a fluid sample(s) using the extracorporeal photoisomerization apparatus of claim 1, and (iii) transferring the fluid sample(s) to one or more fluid chemistry screening devices to test for one or more chemical analytes.

In another preferred embodiment, the process of chemical analysis of mammalian fluids described herein, wherein the fluid screening device(s) tests for one or more of the analytes from the group comprising: creatinine, cholesterol and triglycerides.

In another preferred embodiment, the process of chemical analysis of mammalian fluids described herein, wherein said mammal is a human patient.

In another preferred embodiment, the process of chemical analysis of mammalian fluids described herein, wherein said mammal is not human.

In another preferred embodiment, the process of chemical analysis of mammalian fluids described herein, wherein step (ii) occurs for a period of 1 to 60 minutes per milliliter of fluid In another preferred embodiment, a method of reducing the bilirubin content of mammalian fluid comprising: photoisomerizing a fluid sample by placing said sample in a translucent container, placing said translucent container into the extracorporeal photoisomerization apparatus described herein, and activating the blue light(s) for a period of 1 to 60 minutes per milliliter of fluid.

In another preferred embodiment, the method of reducing the bilirubin content of mammalian fluid described herein, further comprising wherein the blue lights used to reduce bilirubin in the fluid irradiate at a wavelength between 450 to 530 nm.

BRIEF DESCRIPTION OF THE DRAWINGS

FIGS. 1A and 1B are diagrams evidencing the chemical composition of bilirubin and lumiribin, respectively.

DETAILED DESCRIPTION OF THE INVENTION

Figure 2:
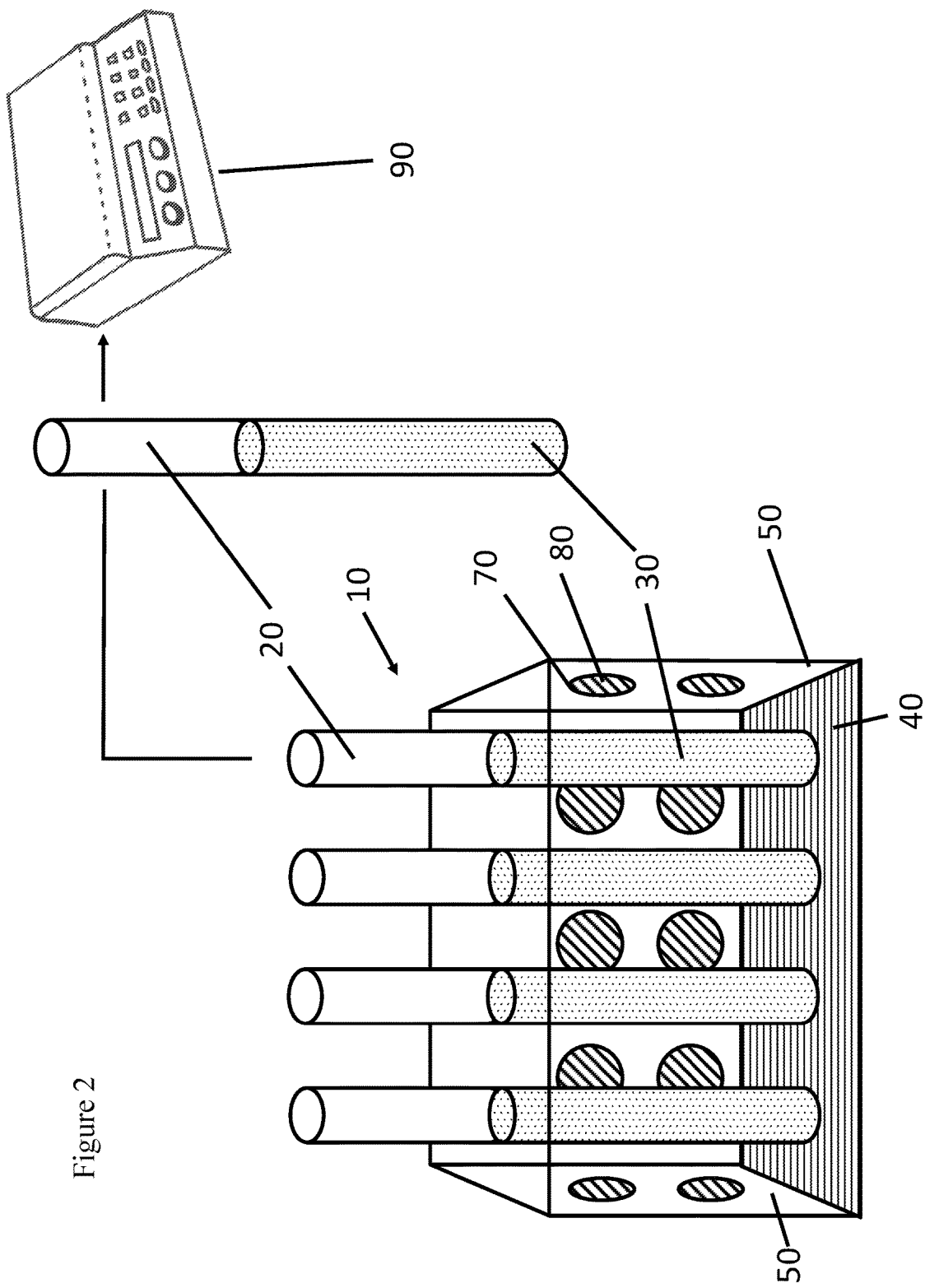
FIG. 2 is a line drawing evidencing a device for photoisomerization of fluid samples as a part of a system including the subsequent chemical analysis of fluid samples.

The invention is an apparatus for the extracorporeal (i.e. outside the body) conversion of bilirubin to isomer molecules, using the process of photoisomerization. Using the apparatus, the irradiation and photoisomerization of bilirubin in body fluid will decrease its concentration, thereby minimizing bilirubin interference on the clinical measurement of other clinical chemical analytes with spectral or chemical properties similar to that of bilirubin.

Bilirubin is a yellow pigment having a molar absorbtivity of about $5 \times 10^4$ as measured at 435 nm. Direct spectrophotometric assay determinations for bilirubin suffer from spectral interferences due to the presence of hemoglobin, which exhibits absorption peaks at 414, 540 and 476 nanometers, and other materials present in bilirubin-containing biological fluids can also cause spectral interferences using direct spectrophotometric assay methods. Excess levels of bilirubin are therefore notorious for causing both spectral and chemical interferences in blood and other fluid samples. A device that can isomerize bilirubin into lumirubin in such samples will overcome many such interferences. Because bilirubin is appreciated globally as a significant source of interference with clinical chemistry tests, various methods have been developed to minimize this interference, but none using blue light.

For example, levels of bilirubin higher than normal chemically affect the enzymatic tests used to detect the presence of glucose, cholesterol and uric acid by decreasing the color of the reaction. Such interference increases with the level of bilirubin in the blood, but become negligible as the bilirubin level decreases to a normal level. Further, bilirubin also overlaps the spectrum of the dye formed in the reaction, causing a positive interference.

Equally problematic is the spectral interference of bilirubin in the determination of metabolites in serum through the Emerson-Trinder chromogenic system, a context in which hyperbilirubinemic samples are found with regularity.

Chemical methods have used potassium ferricyanide or sodium hydroxide to oxidise bilirubin to biliverdin. However, these approaches require additional reagents and steps which introduce variability and time delays into the measurement protocol, as well as increasing the risk of operator error.

Another approach is to install filtration membranes into existing chemistry analyzer machines, although this approach creates a stream of high-turnover filter consumables and requires commitment to one manufacturer for high-cost equipment (for example the IDEXX Catalyst Dx Chemistry Analyzer™) and peripherals.

The competitor approaches mentioned above involve addition of chemical reagents, or installation of filter membranes to reduce bilirubin concentration. Our device avoids these hurdles because it does not require additional reagents or filtration consumables and is agnostic of the lab's existing chemistry analyzer (thereby eliminating the requirement for any specific brand of analyzer or filter membrane). Furthermore the device conducts a rapid photoisomerization reaction on samples which can then be returned to the usual measurement procedure, minimizing the disruption to the lab technician's workflow.

Our approach also yields benefits in operational costs because the device will incorporate LED blue lights which are small, efficient, and long-lived. Commercially-available LED bulbs will be selected in the blue light range appropriate for bilirubin absorption, eliminating unwanted spectral emission (such as ultraviolet). Finally, our device will function equivalently across samples regardless of patient age.

The invention provides an extracorporeal photo-isomerization apparatus for treating bodily fluids from mammals having diseases or conditions associated with abnormal levels of bilirubin, said apparatus comprising: (a) a chamber which holds tubes or containers typically used to store patient samples for clinical chemistry analysis; (b) an array of blue lights in close proximity to the chamber; (c) a power supply; and (d) electronic and/or analog controls to operate the lights.

The invention described also concerns an apparatus for extracorporeal irradiation of a liquid containing bilirubin, with subsequent photo-isomerization of bilirubin. The invention further defines a process for reducing bilirubin concentration in patient fluid samples.

The invention further provides a method for reducing high levels of bilirubin in the blood of a patient comprising: (a) collecting a patient sample; (b) placing said sample in a light-irradiation chamber, thereby photoisomerizing said bilirubin in said sample; and (c) testing the irradiated sample, now cleaned of excess bilirubin, for other chemical analytes per the operator's usual procedure. The direct exposure of patient samples to blue light as described in the instant invention, therefore, would enable the bilirubin photoisomerization reaction, resulting in "clean" blood or other fluid samples for accurate measurement of other chemical analytes.

The extracorporeal bilirubin photoisomerization device described herein irradiates patient samples with blue light, which reduces the concentration of bilirubin thereby decreasing its interference with spectral and chemical measurements of analytes. Upon completion of light irradiation, the patient sample can be returned to the usual protocol for measurement of diagnostic analytes, which often involves the operation of clinical chemistry equipment. No transfer of patient samples into or out of special containers is necessary, thereby minimizing the disruption to the clinical chemistry laboratory's workflow.

The blue lights are chosen for light emission wavelengths of approximately 450 to 530 nm, which is the optimal range of light absorption for bilirubin. In contrast, the optimal range of light absorption for the isomer lumirubin is around 315 m, which constitutes a significant enough differential to prevent lumirubin and other photoisomers from interfering with the measurement of laboratory analytes such as creatinine, cholesterol, enzymatic glucose, uric acid and triglycerides. (See, Journal of Photochemistry and Photobiology B: Biology Vol. 3, Issue 3, June 1989, pp. 419-427.) Lights that emit within approximately 450 to 530 nm are commercially available as fluorescent tubes as well as newer LED (light-emitting diode) bulbs. LED bulbs hold the advantages of lower operational temperatures, reduced power consumption, and long operational lifespan. Current LED bulbs offer an emission intensity of >12 µW/cm2/nm. Indeed, LED exposure (410-490 nm wavelength range) has been shown to be sufficient for bilirubin photoconversion in experimental assays. A pediatric study has suggested that increasing the intensity of blue light exposure will expedite the bilirubin photoconversion reaction, which will shorten the necessary duration of sample irradiation. (See, Fundamentals of phototherapy for neonatal jaundice, Stokowski L A, Adv. Neonatal Car. 2006 December: 6(6): 303-12.) It is recommended that exposure of the skin to blue light surpasses 30 µW/cm2/nm for neonatal hyperbilirubinemia (jaundice). Unlike neonatal bilirubin phototherapy units, however, the present invention places body fluid in close proximity to blue light, allowing direct penetration of light into the bilirubin within the sample. Therefore, even relatively low intensity blue bulbs are likely to be sufficient for bilirubin photoisomerization in the context of the invention.

The blue lights sit in the bottom and/or sides and/or top of the sample irradiation chamber (See, FIG. 2), potentially separated from the patient sample by a clear surface, for example plexiglass, glass or other plastic that is clear and suitable for use. The clear material is chosen to ensure it does not restrict the passage of light rays from blue bulbs toward the body fluid in the sample vessel, and can also serve to protect the invention's lights and/or electric componentry from potential spills or breakage of patient sample tubes. For example, a form of commercially available glass allows ~90% transmission of visible light. However, a clear material such as glass may not be necessary, and patient samples can simply be placed in close proximity to the lights. The patient samples will be positioned to maximize exposure to the light source while avoiding any potential heat transfer issues.

In a preferred embodiment, the fluid samples are exposed to light intensity of at least 6 microWatts per square centimeter per nanometer in the chamber for a period of 1 to 60 minutes per milliliter of fluid. In a more preferred embodiment, the fluid samples are exposed to light intensity of at least 12 microWatts per square centimeter per nanometer in the chamber for a period of 1 to 60 minutes per milliliter of fluid.

In another preferred embodiment, the racks or stands holding sample containers within the device chamber may themselves be translucent glass or plastic, thus providing more complete sample exposure to the photoisomerizing light sources. In a more preferred embodiment, the rack or stand is itself arranged in a geometric configuration to maximize the sample container's exposure to the incoming blue light, such rack or stand holding three or more sample containers in a triangular, square, pentagonal, sextagonal or cylindrical configuration. In another preferred embodiment, the chamber comprises more than four sidewalls, each comprising one or more blue lights, to further increase the level blue light exposure to the samples in the rack or stand, thus speeding the time of isomerization.

The blue lights are electronic devices and thus require a power supply, which can be either alternating current (AC) or direct current (DC) in nature.

DETAILED DESCRIPTION OF THE FIGURES

FIG. 1 comprises chemical diagrams evidencing the conversion of a bilirubin molecule (A) to a lumirubin molecule (B), as initiated by the application of photoisomerization. The bilirubin molecule of (A) contains a hydrophilic domain that is masked by hydrogen bonds, shown by dotted lines. Photo-isomerization, indicated by the arrow, disrupts the hydrogen bonds and converts bilirubin into the lumirubin molecule (B), which is water-soluble due to the newly-opened carboxyl group (C=O), which is available for bonding with water molecules.

FIG. 2 illustrates the extracorporeal photoisomerization of bilirubin in a patient sample utilizing extracorporeal photoisomerization apparatus 10. Patient samples 30 (e.g. blood, plasma, serum) are collected into tubes 20, shown as four upright cylinders in FIG. 2. The samples are held upright within a chamber 100 consisting of a bottom panel 40, at least four upright side panels 50, and an optional, removable top panel 60 (not shown). Blue lights 80 are indicated as emanating through holes 70 cut into the sides 50, and such blue lights will face toward the patient samples 30 in the center of chamber 100. The blue lights irradiate at a wavelength between 450 to 530 nm. The extracorporeal photoisomerization apparatus 10 will have reflective interior sides of the bottom panel 40, side panels 50 and an optional reflective top panel 60 (not shown) which can be lowered to cover the apparatus and to contain and focus the light waves directly onto the patient sample 30, both to increase the speed and efficacy of the photoisomerization process and also to prevent light exposure to the eyes of nearby personnel. The arrow indicates the steps of removing tube 20 containing patient sample 30 from apparatus 10 and its placement in chemical screening device 90, where patient sample 30, now cleared of bilirubin, will be analyzed for levels of chemical analyte(s) for diagnostic or other medical purposes.

Figure 3:
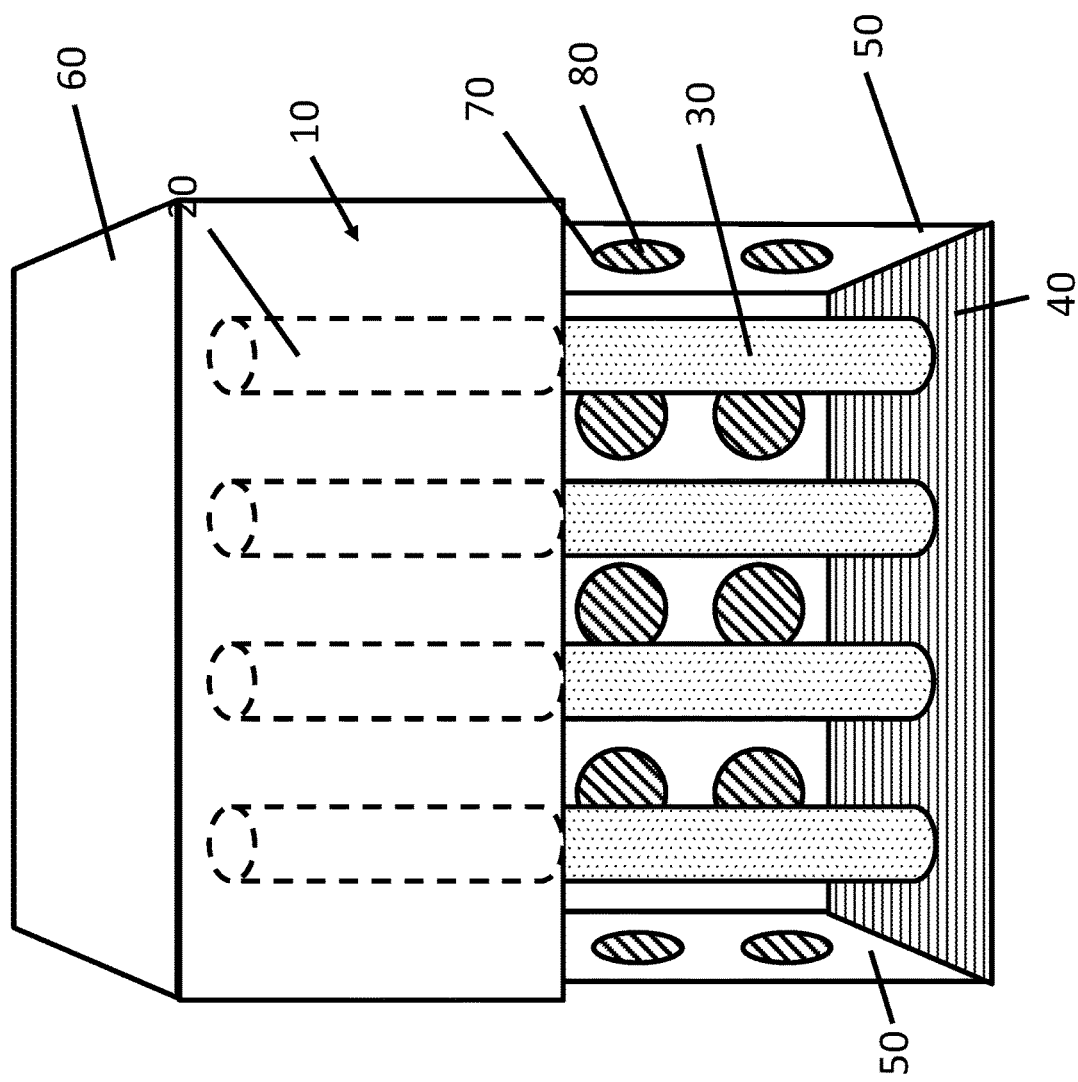
FIG. 3 is a line drawing evidencing the device of FIG. 2 evidencing a top panel and utilizing broken lines to show the tubes covered by the top panel.

FIG. 3 illustrates the extracorporeal photoisomerization of bilirubin in a patient sample utilizing extracorporeal photoisomerization apparatus 10 as a part of a mammalian fluid chemical analysis process 100. Extracorporeal photoisomerization apparatus 10 is pictured as in FIG. 2, with the inclusion of top panel 60, shown on a see-through basis indicating top panel 60's coverage of tubes 20.

Figure 4:
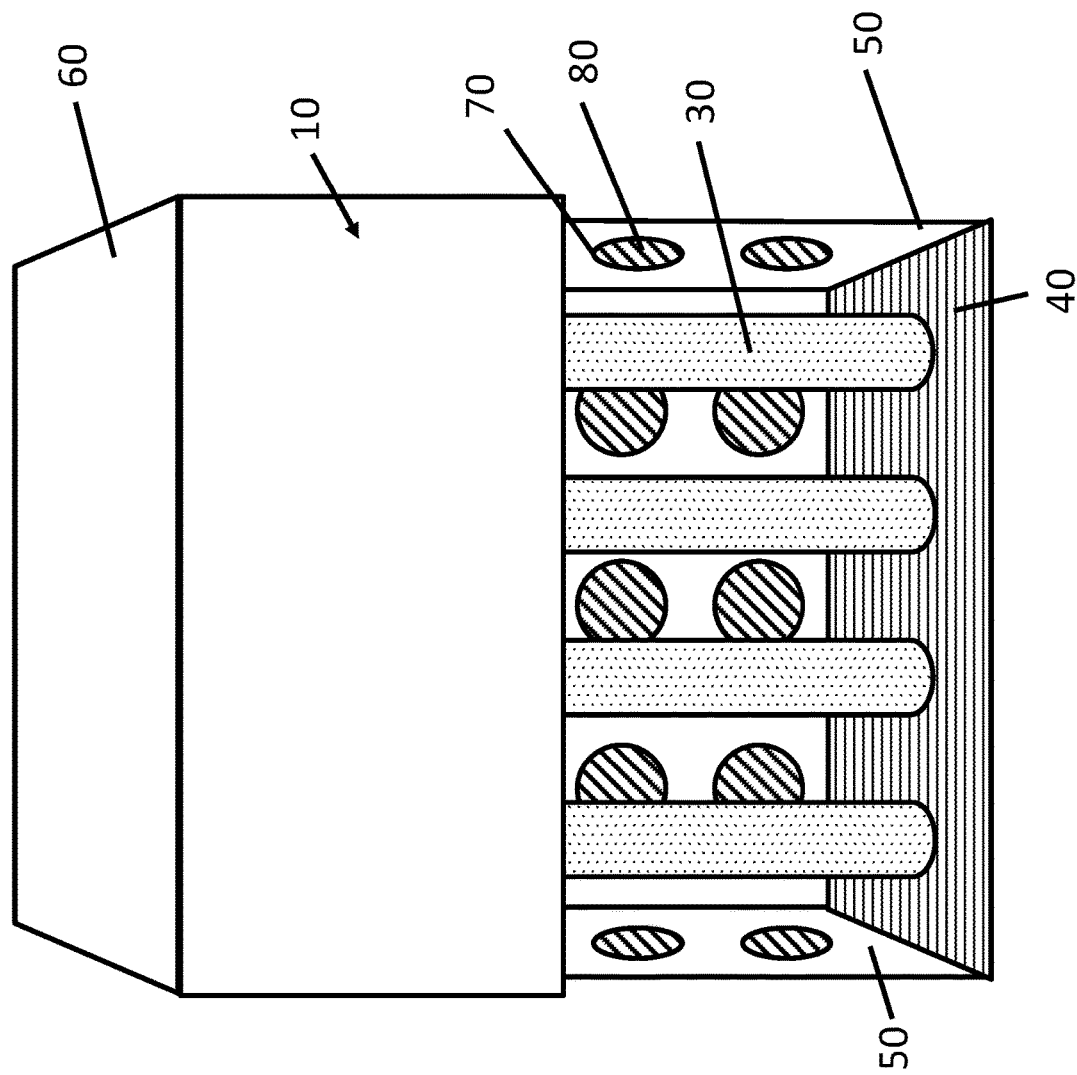
FIG. 4 is a line drawing evidencing the device of FIG. 2 evidencing a top component.

FIG. 4 is the same as FIG. 3, but with the top panel 60 shown as opaque.

LIST OF REFERENCE NUMBERS 10 extracorporeal photoisomerization apparatus
20 tube
30 patient sample
40 bottom panel
50 side panels
60 top panel
70 holes
80 blue lights
90 chemical screening device
100 mammalian fluid chemical analysis process The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable equivalents.

We claim:

1. A method of reducing the bilirubin content of mammalian fluid comprising: (i) converting all or a portion of a bilirubin component of a fluid sample taken from a mammal into isomer molecules by (ii) placing said sample in a translucent container, placing said translucent container into an extracorporeal photoisomerization apparatus comprising a chamber consisting of a bottom panel and at least four side panels having reflective interior surfaces, wherein one or more of the bottom panel and/or side panels comprises one or more holes, an LED blue light centered within each such hole and facing towards the interior of the chamber, one or more stands configured within the chamber to hold containers of fluid for irradiation, a means for turning the LED blue light(s) on or off, and a means for delivering electricity to the one or more blue lights, (iii) activating the blue light(s) for a period of 1 to 60 minutes per milliliter of fluid, and (iv) transferring the fluid sample with its reduced bilirubin component to one or more fluid chemistry screening devices to test for one or more chemical analytes normally obscured by bilirubin.

2. The method of claim 1, wherein the blue lights irradiate at a wavelength between 450 to 530 nm.

3. The method of claim 1, wherein further comprising wherein the blue lights irradiate at a wavelength between 450 to 530 nm.

4. The method of claim 1, wherein further comprising wherein the blue lights irradiate at a light intensity level of at least 6 microWatts μW/cm2/nm of light wavelength.

5. The method of claim 1, wherein the fluid screening device(s) tests for one or more of the analytes from the group comprising: creatinine, cholesterol and triglycerides.

* * * * *